(12) United States Patent
Varis

(10) Patent No.: US 7,302,311 B2
(45) Date of Patent: *Nov. 27, 2007

(54) CARTRIDGE FOR DISPENSING PILL- OR CAPSULE-FORM MEDICATIONS IN DESIRED DOSES

(75) Inventor: Reijo Varis, Helsinki (FI)

(73) Assignee: ADDOZ OY, Helsinki (FI)

( * ) Notice: Subject to any disclaimer, the term of this patent is extended or adjusted under 35 U.S.C. 154(b) by 0 days.

This patent is subject to a terminal disclaimer.

(21) Appl. No.: 11/338,272

(22) Filed: Jan. 24, 2006

(65) Prior Publication Data

US 2006/0144846 A1 Jul. 6, 2006

Related U.S. Application Data

(63) Continuation of application No. 10/790,372, filed on Mar. 1, 2004, now Pat. No. 6,988,634, which is a continuation of application No. 10/369,924, filed on Feb. 19, 2003, now Pat. No. 6,702,146.

(51) Int. Cl.
*G06F 17/00* (2006.01)

(52) U.S. Cl. ............... 700/232; 700/237; 700/243; 221/2; 221/7; 221/9; 221/15

(58) Field of Classification Search ............ 221/2, 221/3, 7, 15; 700/236, 237, 242, 243
See application file for complete search history.

(56) References Cited

U.S. PATENT DOCUMENTS 3,815,780 A 6/1974 Bauer 4,674,651 A 6/1987 Scidmore et al.
4,695,954 A 9/1987 Rose et al.
4,768,176 A 8/1988 Kehr et al.

(Continued)

FOREIGN PATENT DOCUMENTS

WO   WO 95/28142   10/1995

(Continued)

*Primary Examiner*—Gene O. Crawford
*Assistant Examiner*—Timothy Waggoner
(74) *Attorney, Agent, or Firm*—Klauber & Jackson L.L.C.

(57) ABSTRACT

A system for dispensing pill- or capsule-form medications (61) in desired doses (60). The system comprises a dispensing device (35), which includes a cartridge (20, 40) rotatable relative to a housing or frame (10) and provided with discrete dosage compartments (27, 47) for desired doses of medication. The cartridge (20, 40) is manipulated by elements (18, 18a, 18b; 14a, 14b, 15, 18, 19), whereby each separate dosage compartment (27, 47) is rotatable relative to the housing or frame (10) to a dispensing point (4, 12) for the dose of medication (60). A signalling device (75, 76) producing a sound and/or light signal activates at preprogrammed times. An electronics unit (19, 55) containing a dispensing program is reprogrammable by means of an external programming device (36, 66, 101, 102). The cartridge (20, 40) is adapted to be disengaged from the dispensing device (35) and to be transferred to a loading device (80), which fills the dosage compartments (27, 47) of the cartridge with desired doses of medication and furnishes the filled cartridge with identification data (ID), on the basis of which the filled cartridge (20, 40) can be certifiably returned to the proper dispensing device (35), which is arranged to upkeep a dispensing event log at a distant control file (64a).

17 Claims, 4 Drawing Sheets

U.S. PATENT DOCUMENTS

| | | |
|---|---|---|
| 4,785,969 A | 11/1988 | McLaughlin |
| 4,911,327 A | 3/1990 | Shepherd et al. |
| 5,176,285 A | 1/1993 | Shaw |
| 5,372,276 A | 12/1994 | Daneshvar |
| 5,392,952 A | 2/1995 | Bowden |
| 5,490,610 A | 2/1996 | Pearson |
| 5,564,593 A | 10/1996 | East, Sr. |
| 5,710,551 A | 1/1998 | Ridgeway |
| 5,805,051 A | 9/1998 | Herrmann et al. |
| 5,971,594 A | 10/1999 | Sahai et al. |
| 6,021,918 A * | 2/2000 | Dumont et al. .......... 221/2 |
| 6,075,755 A | 6/2000 | Zarchan |
| 6,145,697 A * | 11/2000 | Gudish .......... 221/3 |
| 6,198,383 B1 | 3/2001 | Sekura et al. |
| 6,401,991 B1 * | 6/2002 | Eannone .......... 221/12 |
| 6,510,962 B1 * | 1/2003 | Lim .......... 221/15 |
| 6,702,146 B2 * | 3/2004 | Varis .......... 221/3 |
| 2001/0009398 A1 | 7/2001 | Sekura et al. |

FOREIGN PATENT DOCUMENTS

| | | |
|---|---|---|
| WO | WO 97/43999 | 11/1997 |
| WO | WO 99/43284 | 9/1999 |

* cited by examiner

CARTRIDGE FOR DISPENSING PILL- OR CAPSULE-FORM MEDICATIONS IN DESIRED DOSES

CROSS REFERENCE TO RELATED APPLICATIONS

The present application is a Continuation of U.S. application Ser. No. 10/790,372 filed Mar. 1, 2004 now U.S. Pat. No. 6,988,634, which is in turn, a Continuation of application Ser. No. 10/369,924 filed on Feb. 19, 2003 now U.S. Pat. No. 6,702,146. Applicants claim the benefits of 35 U.S.C. § 119 as to the said United States applications, and the entire disclosure of said applications is incorporated herein by reference in its entirety.

The invention relates to a cartridge for dispensing pill- or capsule-form medications in desired doses, said cartridge comprising individual dosage compartments for desired doses of medication, rotated to coincide with any of the dosage compartments for loading and/or dispensing of doses through the opening, and means for visual indication of dispensing schedule.

It is an object of the invention to provide a dispensing cartridge for doses of medication, which can be used either as a manually operated dispensing cartridge or with an intelligent dispensing device.

Still another object of the invention is to use a dispensing cartridge which facilitates filling or loading of the dosage compartments by doses of medication either manually or more or less in an automated manner by using a loading robotics, and which dispensing cartridge alone can also be used as a simple manually operated dispensing apparatus which is provided by visual indication of dispensing schedule, said visual indication serving both for manual filling or loading and for manually operated dispensing if the cartridge is used alone as a manually operated dispensing apparatus.

Still a further object of the invention is to provide, as a preferred option, a possibility to fill or load the dosage compartments of the dispensing cartridge under control of a computer program which gives an alarm if there are non-compatible medications to be loaded.

Still a further object of the invention is to provide a medication dispensing system wherein the information of identification, medication and dispensing schedule follows the cartridge and can be easily re-programmed and transferred between the cartridge and the memory of the dispensing device containing the dispensing program, as well as between either of these and a programming computer.

This and other objects are achieved according to the invention on the basis of the characterizing features set forth in the annexed claim 1. The non-independent claims disclose preferred embodiments of the invention, which facilitate dosing or loading logistics, offer versatile re-programming possibilities for dispensing, and facilitate the supervision of medication.

A preferred embodiment of the present invention will now be described in more detail with reference made to the accompanying drawings, in which:

FIG. 3 shows a programming device useful between the dispensing device and a facility computer in hospital, rest home or the like.

Figure 1:
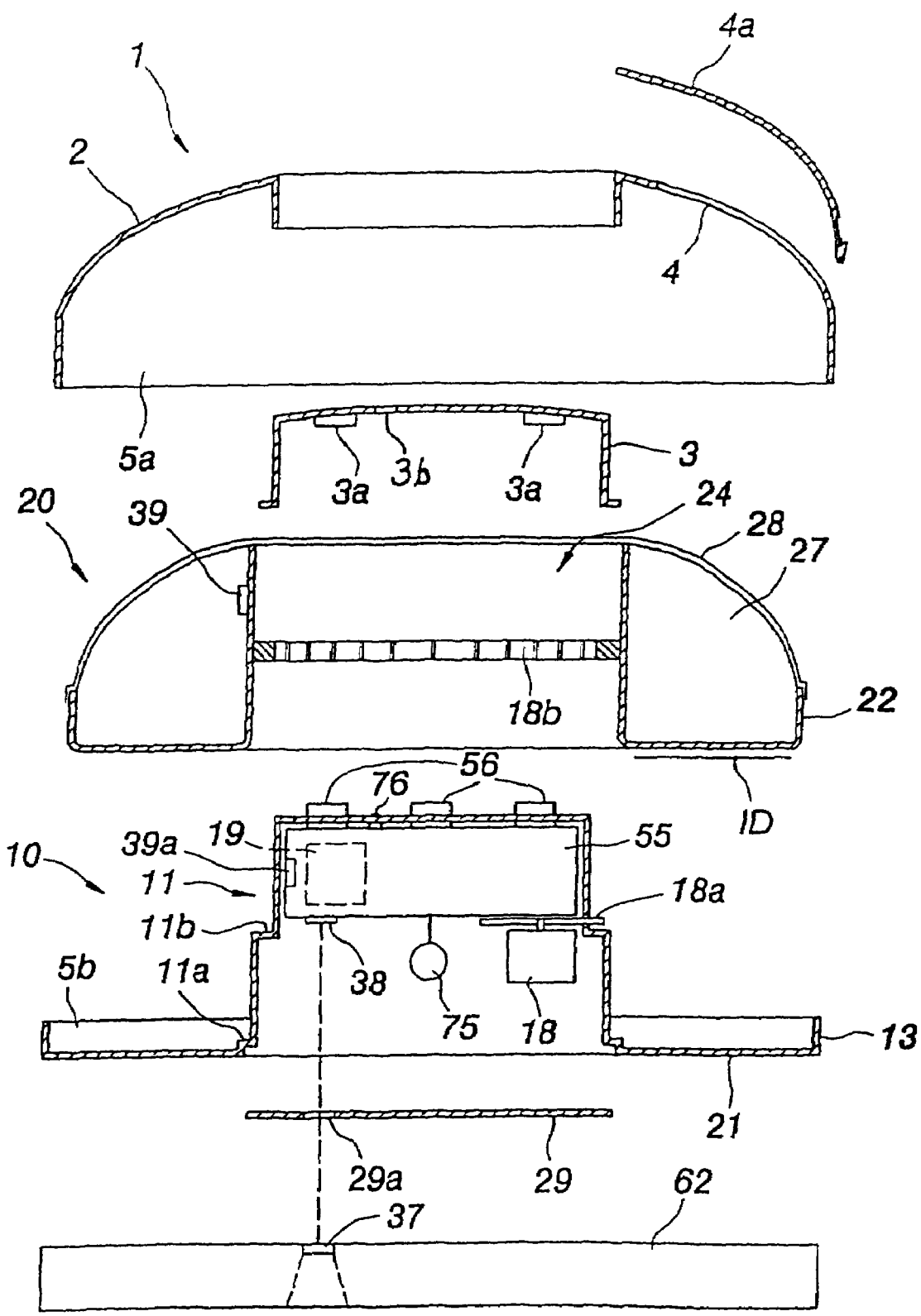
FIG. 1 shows schematically a medication dispenser according to an embodiment useful as part of a system of the invention.

The prescription controlling the loading device 80 in terms of its filling action is adapted to be delivered, along with a patient's identification data, by way of a communication network, such as the internet 65 or a chip card 68, to a computer 67 controlling operation of the loading device 80. Alternatively, the prescription can be delivered conventionally on a paper printout, from which the necessary information is transferred by typing to the computer 67 controlling the dosage.

The cartridges 20, 40 are adapted to be disengaged from the dispensing device 35 and to be transferred to the loading device 80 for filling or loading the dosage compartments 27, 47 of a cartridge with desired doses of medication. In addition, the mechanism 73 associated with the loading device 80 furnishes the loaded cartridge 20 with identification data ID, on the basis of which the loaded or filled cartridge 20, 40 can be certifiably returned to the correct dispensing device 35.

The dispensing device 35 has its program electronics 19 re-programmable with an external programming unit. In the depicted case, the external programming unit comprises a mobile telephone 36, whereby a dispensing program or its updatings can be fed to the program electronics 19 by way of an IR link 37, 38 shown in FIG. 8. The external programming unit for a dispensing program may also comprise the facility computer 66, which has a communication via the internet 65 with the control file 64a or which has the control file stored in its bulk memory. In the latter case, the dispensing device 35 can be brought to the IR link 138 (shown in FIG. 10) of the computer 66 for programming or the program can be transferred from the computer 66 to the mobile phone 36, whereby the program is delivered further to the program memory 19 of the dispensing device 62.

The cartridge 20, 40 can be furnished with identification data, e.g. by attaching to the cartridge an identification-data carrying label ID by means of the mechanism 73. Optionally or additionally, the identification can be certified.

The following description deals in more detail with the dispensing device shown in FIG. 1. The dispensing device is provided with a cover or housing 1, comprising a shell portion 2 which includes a dispensing outlet 4 and a flap 4a for closing the same, if necessary. The components 2 and 4a can be manufactured in moulded plastics and at least the flap 4a is transparent (shell portion 2 may be non-transparent). The flap 4a may have its base hinged in such a way that the flap 4a can be removed as required, if a patient finds it difficult to operate a locking mechanism attached to its outer end. A push button 3 fits in a central hole in the shell portion 2 and is manufactured from transparent stained plastics. The colour of the push button 3 can also be used for encoding a loading device. The push button 3 is provided with a transparent window (not shown) for monitoring a timer display (the window can be covered as required). In addition, the push button 3 is provided with an opening 3b for a led light indicator 76.

The cartridge 20 comprises preferably a transparent machine-washable plastic manufactured in food-grade plastics. The cartridge is provided with 28 dosage compartments 27 for tablets. The cartridges 20 are interchangeable between various dispensing devices. The cartridge has its central hole 24 provided with a gear rim 18b, which supplies the cartridge with its rotary drive from a gearwheel 18a of the motor 18 placed in the central hollow of the housing 10 (the necessary gear between the motor 18 and the gearwheel 18a has not been shown).

The housing 10 is manufactured in transparent plastics e.g. as a plastic extrudate. Consequently, a prescription or an identification tag ID, attached to the bottom of the cartridge 20, is visible as required through a transparent floor 21 of the housing 10. Through a rim collar 13 of the housing it is possible to visually observe medications remaining in the dosage compartments 27 of a cartridge (even in the case that the shell portion is non-transparent).

An electronics unit 55 is disposed inside a cylindrical central hollow 11 within the housing 10. The electronics unit is provided with a memory-equipped, programmable processor 19, which can be programmed with four daily times for medication by means of key buttons 56 or an IR link 37, 38 included in the unit 55. In addition, the program takes care of necessary safety times and delay times, as well as a deadline for the ingestion of a dose. The IR link 37, 38, included in the unit 55, along with the GSM module 62, serving as an accessory, enables a telecontrol over medication and eventual alarms regarding malfunctions. Hence, the program takes care of the specification-compliant function of a dispensing device and, merely by modifying the program, it is possible to develop various versions of a dispensing device. Naturally, the IR link can be replaced with an RF link or other links operating in compliance with standards.

A floor panel 29, having a hole 29a for the operation of an IR link, encloses the housing hollow 11 which has space also for a sound signal device 75 and a battery.

The motor 18 comprises e.g. a stepped motor, which activates its operation upon pressing down the push button 3 as pins 3a depress the programming keys 56 of the electronics unit 55. However, this activation only occurs after the signaling device 75, 76 has been activated under the control of program electronics 19, 55. Every time the elements 18, 18a operating the cartridge 20 are activated, the information about a dispensing occurrence is transmitted to a distant control file, which comprises e.g. a www-page in the internet and which constitutes a monitoring log for taking the medication. Optionally, a memory associated with the program electronics 19, 55 is used to collect information about dispensing occurrences and to transmit the same at prescribed times to said control file.

Thus, the electronics unit 55 included in the dispensing device is programmable either by a patient him- or herself or by medical personnel (keys 56) or by means of the computer 66 or utilizing an IR link 138 in the programming device 101 or 102, or in the GSM telephone. According to its programming, the dosage dispenser electronics 19, 55, 75, outputs a signal to the user whenever it is time for medication and prevents the ingestion of any dose of medication other than the one to be taken at that precise time.

As the dosage cartridges 20 containing doses of medication are carried independently of a dispensing device from the loading device 80 to the dispensing device 35, the dosage cartridge 20 must be provided with a cover 28. This cover 20 may be a rotatable cover of thin transparent plastics, which is provided by a loading opening 28a (FIG. 2) for manual loading. The cover 28 is removed as the cartridge 20 is inserted in the housing 10. The cartridge turns an angular distance equal to the dosage compartment 27 every time the push button 3 is depressed at the accepted medication time. The stepped motor 18 can be used for the precise determination of an angle of rotation in such a way that, even after quite a long-term use, the dosage compartments 27 always coincide with the dispensing outlet 4.

Figure 2:
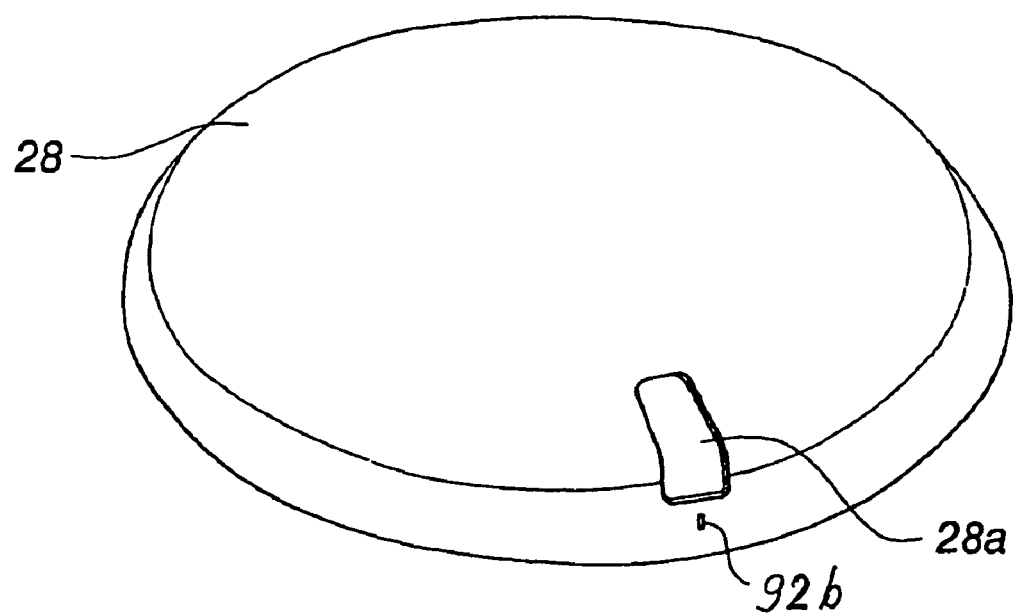
FIG. 2 shows a dosage cartridge for the dispenser of FIG. 1 or without the dispenser as a manually operated dispensing cartridge.
Figure 2:
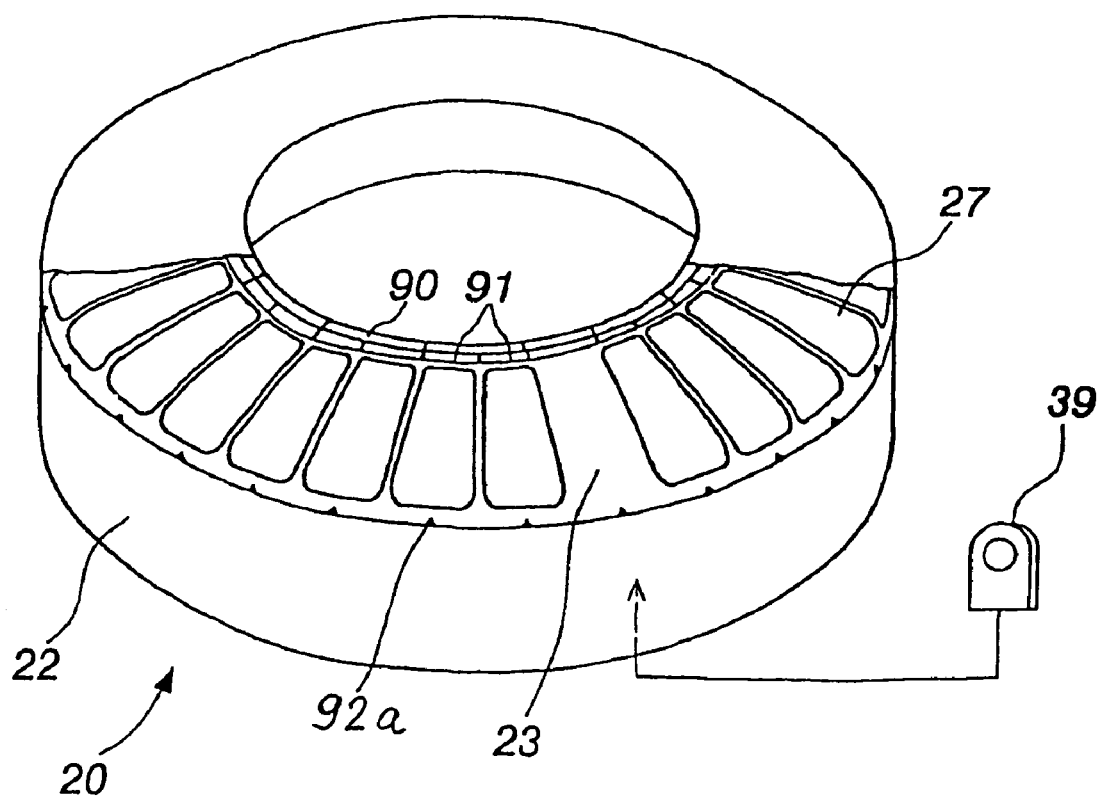
Figure 3:
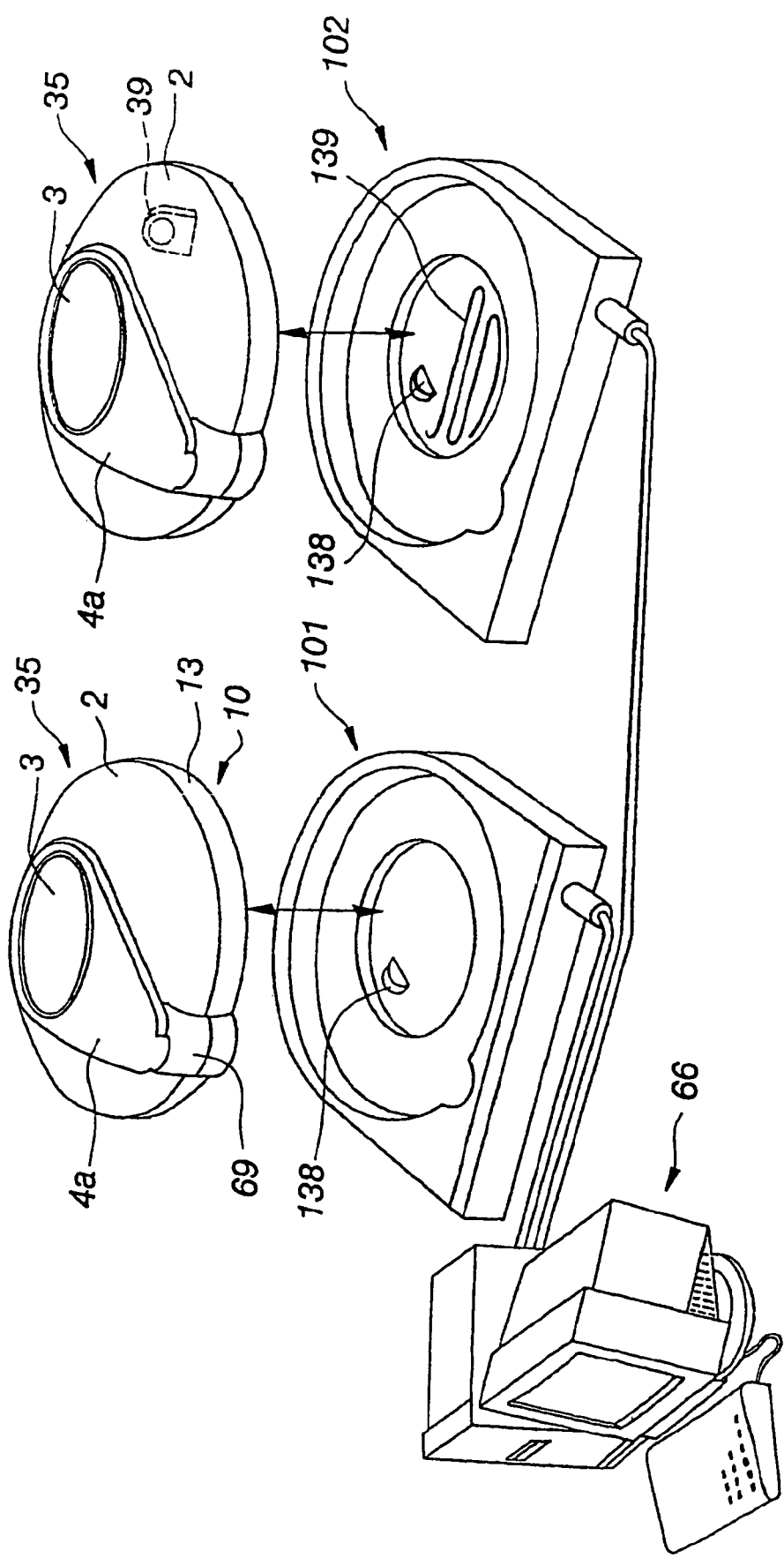

As shown in FIG. 2, mechanical detents 92a around the periphery of the cartridge 20 can be used to fit with a complementary detent 92b in the cover 28 to slightly hold the rotation of the cover 28 each time the opening 28a coincides with the dosage compartment 27.

FIG. 2 illustrates a section from the rim of a cartridge (the rest of the rim being also provided by compartments 27 though not shown). The dosage compartments 27 are narrow and high so as to accommodate 28 of those along a relatively small circular arc. This configuration is beneficial in terms of both elongated capsules and circular pills. Between the dosage compartments 27 is a vacant recess or space 23 and in line therewith the dispenser bottom 10/21 is provided with a protrusion (not shown), which is insertable in the space 23 (from the bottom side thereof) as an indication for inserting the cartridge 20 in the housing 10 of the dispensing device 35 (and similarly in the loading device 80) in a preset initial position. The cartridge 20 rests upon setbacks 11b and 11a included in the cylindrical housing hollow 11. Space 23 can be utilized also for receiving the RF-tag 39.

The jacket or shell portion 2 has a bottom edge which can be locked with an appropriate forming to the top edge of an outer housing rim 13. In view of switching the cartridges 20, there must be an engagement between the jacket 2 and the housing 10 which is readily disconnectable and reconnectable (if necessary, also lockable). This can be implemented e.g. by forming the opposing edges with a combination of short threading and bayonet coupling. A lock cylinder may be placed inside the protrusion 69.

As shown in FIG. 2, there is a schedule ring 90, 91 close to the inner rim of the openings of the dosage compartments 27. This schedule ring is a replaceable paper or plastic ring having a first ring divided into sections 90, each section 90 corresponding to a certain day of a week typed in the corresponding section 90. Such a "week day section" covers 1-4 compartments 27. A second ring is divided into subsections 91 of the "week day sections" 90, indicating first, second etc. medicine of a day. With this kind of scheduling ring and the rotatable cover 28 with opening 28a, the cartridge can also be used as a manually operated dispensing cartridge also without the actual dispensing device. This is a clear benefit of the cartridge construction, which facilitates the manual loading in one hand, but enables automated loading on the other hand, and is furthermore applicable to be used with or without the intelligent dispensing device.

Figure 4:
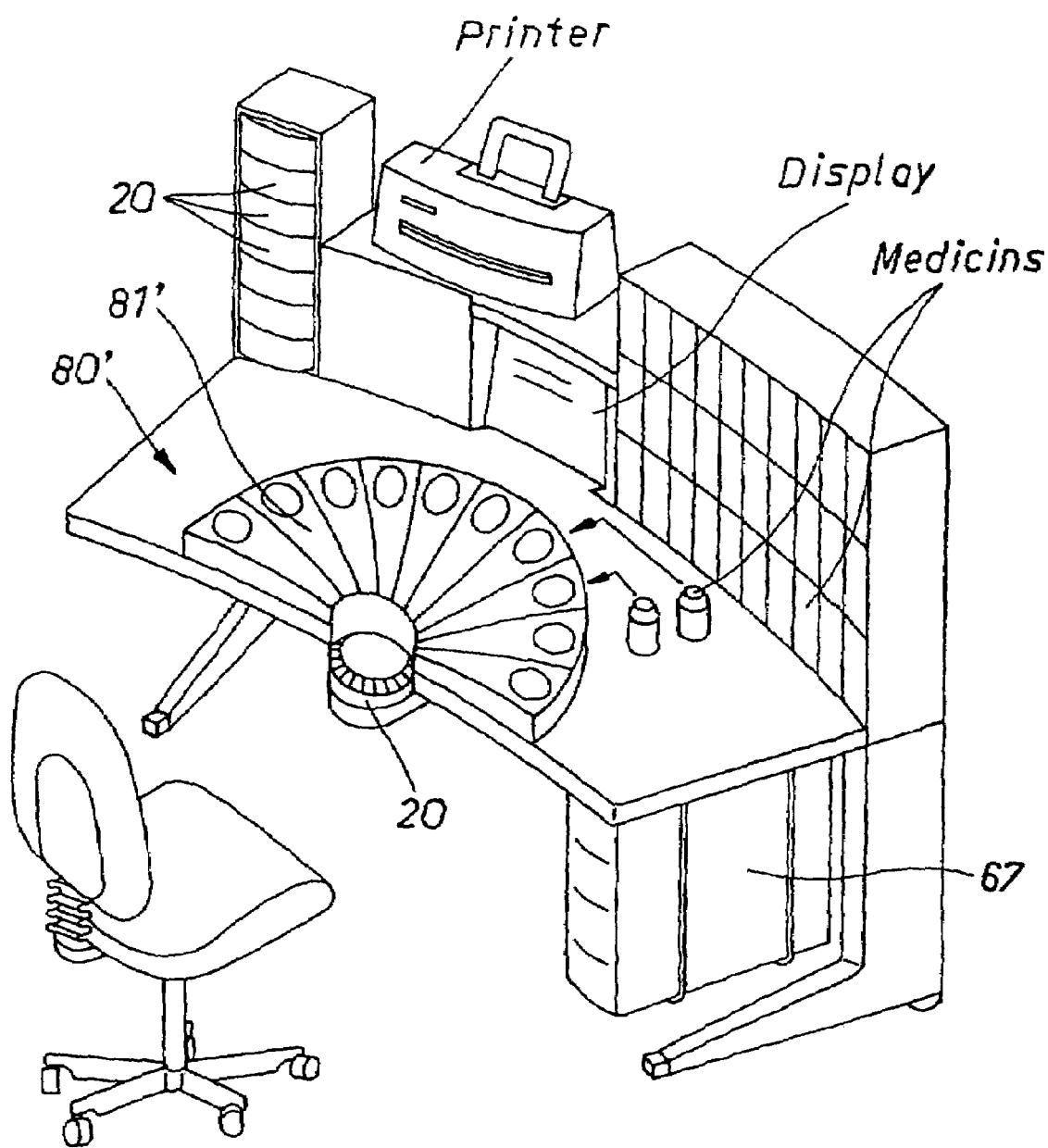
FIG. 4 illustrates a schema of a loading device located for example in a dispensary or druggist's.

FIG. 4 shows a semi-automatic loading device 80' having feeders 81' arranged in a semi circle from medicine receptacles to the periphery of cartridge 20 which is rotated automatically under control of the computer 67 and the prescription fed in the computer 67. The cartridges 20 are manually changed and the medicine receptacles are manually filled. Also in this case it is important to provide each and every cartridge 20 with the identification label ID and/or with the RF-tag bearing the identification information. Preferably, at least an optically readable ID label is attached to the cartridge by means of the loading device 80, 80'.

As can be learned from the above description the invention serves an advanced logistics for delivering medicines from dispensary to the users (patients) and for efficient monitoring of appropriate use or disposition of the medicines.

The invention claimed is:

1. An intelligent dispensing device (35) for dispensing pill- or capsule-form medications in desired doses, said dispending device comprising a housing or frame (10), a cartridge (20), rotatably supported on the housing or frame (10), said cartridge comprising individual dosage compartments (27) for desired doses of medication, the cartridge (20, 40) being adapted to be disengageable and removable from the dispensing device (35) for filling the dosage compartments (27) of the cartridge with desired doses of medication, a signalling device (75, 76) giving a sound and/or light signal, which activates at pre-programmed points of time, and an electronics unit (19, 55) containing program electronics (19) and a dispensing program, the program electronics (19) being re-programmable by means of push buttons (56) or with a programming device (66, 101, 102), the dispensing being arranged to be effected by means of the users own action which is exerted onto the dispensing device (35), means (18, 18a) for rotating the cartridge (20), the rotating means being activated to function upon pressing a push button (3), but only during a predetermined time window for taking the medication, a cover (2) mountable around the frame (10), at least one cartridge (20) being encloseable within a space (5a, 5b) defined by the cover (2) and the cartridge (20).

2. A loading device for loading cartridges as set forth in claim 1, characterized in that the cartridge is insertable into a separate closing or loading device (80) for filling the dosage compartments (27) of the cartridge with desired doses of medication and for furnishing the filled cartridge (20) with identification data (ID).

3. A loading device as set forth in claim 2, characterized in that the prescription controlling the loading device (80) in terms of its filling action is adapted to be delivered, along with a patient's identification data, to a computer (67) controlling operation of the loading device (80).

4. A loading device as set forth in claim 2, characterized in that the loading device (80) is adapted to provide the cartridge (20) with an optically readable label (ID) disclosing the identification data.

5. A loading device as set forth in claim 3, characterized in that the loading device (80) is adapted to provide the cartridge (20) with an optically readable label (ID) disclosing the identification data.

6. A loading device as set forth in claim 2, characterized in that the cartridge (20) carries an electronic identification tag (39), which the loading device (80, 80') furnishes with identification data for a customer, and that the dispensing device (35) or a hospital dispensary is provided with elements (39a; 102/139) for reading the data disclosed in the identification tag (39).

7. A dispensing device as set forth in claim 1, characterized in that the electronics unit (19, 55) involves a memory which collects information regarding dispensing occurrences and transmits the same at prescribed times to a control file, which compiles a monitoring log of taking a medication, the prescribed times being short enough for practically real time monitoring of taking a medication.

8. A dispensing device as set forth in claim 1, characterized in that the electronics unit (19, 55) containing a dispensing program is programmable by means of push buttons (56) included therein.

9. A dispensing device as set forth in claim 1, characterized in that between the dosage compartments (27) of the cartridge (20) is a vacant recess or space (23) and the housing or frame (10) of the dispensing device is provided with a protrusion, which functions as a response and/or an indication for inserting the cartridge (20) in the housing or frame (10) of a dispensing device in a preset initial position.

10. A dispensing device as set forth in claim 1, characterized in that a motor (18) rotates the cartridge (20) in compliance with a program programmed in a programmable memory of the electronics unit (19, 55).

11. A dispensing device as set forth in claim 1, characterized in that a motor (18) rotates the cartridge (20) through an angular distance equal to the dosage compartment (27) as the dispensing button (20) is pressed at the accepted medication time, which is programmed in the program of the electronics units (19, 55).

12. A dispensing device as set forth in claim 1, characterized in that the programming device (66, 101, 102) is an external device, which has a wireless communication link (37, 138) with the electronics unit (19, 55) of the dispensing device (35).

13. A dispensing device as set forth in claim 12, characterized in that the external programming device (66, 101, 102) for a dispensing program comprises a programming device (101, 102) equipped with a wireless link (38, 138) for feeding the dispensing program, or modifications thereto to the electronics unit (19, 55).

14. A dispensing device as set forth in claim 12, characterized in that the external programming device (66, 101, 102) for a dispensing program comprises a computer (66), which has a link via the internet to a distant control file or which has a control file stored in its bulk memory.

15. A dispensing device as set forth in claim 1, characterized in that upon every activation of the means (18, 18a) manipulating the cartridge (20), the information about a dispensing occurrence is transmitted to a control file (64a), which compiles a monitoring log of taking a medication.

16. A dispensing device as set forth in claim 1, characterized in that the cartridge (20,40) is furnished with identification data (ID), on the basis of which the filled cartridge (20) can be certifiably returned to the proper dispensing device (35).

17. A dispensing device as set forth in claim 1, further comprising a removable cover (28) for closing the dosage compartments when the filled cartridge is outside the dispensing device.

* * * * *